US007528245B2

(12) United States Patent
Hu

(10) Patent No.: US 7,528,245 B2
(45) Date of Patent: *May 5, 2009

(54) EFFICIENT PROTEIN EXPRESSION SYSTEM

(75) Inventor: Mary ChaoHong Hu, Bothell, WA (US)

(73) Assignee: ID Biomedical Corporation of Washington, Philadelphia, PA (US)

( * ) Notice: Subject to any disclaimer, the term of this patent is extended or adjusted under 35 U.S.C. 154(b) by 292 days.

This patent is subject to a terminal disclaimer.

(21) Appl. No.: 11/209,589

(22) Filed: Aug. 22, 2005

(65) Prior Publication Data

US 2005/0287642 A1 Dec. 29, 2005
US 2007/0148731 A9 Jun. 28, 2007

Related U.S. Application Data

(63) Continuation of application No. 10/284,083, filed on Oct. 28, 2002, now Pat. No. 6,939,959.

(60) Provisional application No. 60/348,434, filed on Oct. 26, 2001.

(51) Int. Cl.
C12N 15/67 (2006.01)
C12N 15/68 (2006.01)
C12N 15/72 (2006.01)
C12N 15/11 (2006.01)
C12P 21/00 (2006.01)

(52) U.S. Cl. .................. 536/24.1; 435/69.1; 435/320.1; 435/325; 435/471; 435/348; 435/419

(58) Field of Classification Search .................. None
See application file for complete search history.

(56) References Cited

U.S. PATENT DOCUMENTS

| 4,495,280 | A | 1/1985 | Bujard et al. ............... 435/6 |
|---|---|---|---|
| 4,868,111 | A | 9/1989 | Bujard et al. ............... 435/68 |
| 5,350,690 | A | 9/1994 | Zukowski .............. 435/252.31 |
| 5,689,056 | A | 11/1997 | Cramer et al. ............. 800/205 |
| 5,756,347 | A | 5/1998 | Sugimoto et al. ......... 435/320.1 |
| 5,876,962 | A | 3/1999 | Bishop et al. ............. 435/69.1 |
| 5,985,285 | A | 11/1999 | Titball et al. ............. 424/234.1 |
| 6,063,386 | A | 5/2000 | Dale et al. ............... 424/244.1 |
| 6,194,168 | B1 | 2/2001 | Gentz et al. ............... 435/69.1 |
| 6,291,245 | B1 | 9/2001 | Kopetzki et al. ............ 435/471 |
| 6,436,639 | B1 | 8/2002 | Kiefer et al. ................ 435/6 |
| 6,716,433 | B1 | 4/2004 | Dale ....................... 424/244.1 |
| 2003/0143245 | A1 | 7/2003 | Reddish et al. ........... 424/190.1 |
| 2005/0063988 | A1 | 3/2005 | Dale ..................... 424/190.1 |
| 2005/0202037 | A1 | 9/2005 | Dale ..................... 424/190.1 |

FOREIGN PATENT DOCUMENTS

WO WO 94/06465 3/1994
WO WO 99/16858 4/1999

OTHER PUBLICATIONS

Briat, J.-F. et al., "Identification and characterization of a new transcriptional termination factor from *Escherichia coli*," *Proc. Natl. Acad. Sci. USA* 81: 7373-7377, Dec. 1984.

Brosius, J. et al., "Gene Organization and Primary Structure of a Ribosomal RNA Operon from *Escherichia coli*," *J. Mol. Biol.* 148(2): 107-127, May 15, 1981.

Casadaban, M.J. et al., "Analysis of Gene Control Signals by DNA Fusion and Cloning in *Escherichia coli*," *J. Mol. Biol.* 138(2): 179-207, Apr. 5, 1980.

De Boer, H.A. et al., "A Hybrid Promoter and Portable Shine-Dalgarno Regions of *Escherichia coli*," *Biochem. Soc. Symp.* 48: 233-244, 1983.

Dunn, J.J. et al., "The transcription termination site at the end of the early region of bacteriophage T7 DNA," *Nucleic Acids Research* 8(10): 2119-2132, May 24, 1980.

Ehrlich, S.D. et al., "DNA cloning in *Bacillus subtilis*," *Proc. Natl. Acad. Sci. USA* 75(3): 1433-1436, Mar. 1978.

Gilman, M.Z. et al., "Nucleotide sequence of two *Bacillus subtilis* promoters used by *Bacillus subtilis* sigma-28 RNA polymerase," *Nucleic Acids Research* 9(2): 5991-6000, 1981.

Grange, T. et al., "Expression of the mouse dihydrofolate reductase cDNA in *B. subtilis*: a system to select mutant cDNAs coding for methotrexate resistant enzymes," *Nucleic Acids Research* 12(8): 3585-3601, 1984.

Gryczan, T.J. et al., "Characterization of *Staphylococcus aureus* Plasmids Introduced by Transformation into *Bacillus subtilis*," *Journal of Bacteriology* 134(1): 318-329, Apr. 1978.

Hawley, D.K. et al., "Compilation and analysis of *Escherichia coli* promoter DNA sequences," *Nucleic Acids Research* 11(8): 2237-2255, 1983.

Jay, E. et al., "High-level expression of a chemically synthesized gene for human interferon-γ using a prokaryotic expression vector," *Proc. Natl. Acad. Sci. USA* 81(8): 2290-2294, Apr. 1984.

Kreft, J. et al., "Recombinant Plasmids Capable of Replication in *B. subtilis* and *E. coli*," *Molec. gen. Genet.* 162: 59-67, 1978.

Lee, G. et al., "Nucleotide Sequence of a Promoter Recognized by *Bacillus subtilis* RNA Polymerase," *Molec. gen. Genet.* 180(1): 57-65, 1980.

Lee, G. et al., "Transcription of Cloned DNA from *Bacillus subtilis* Phage SP01 Requirement for Hydroxymethyluracil-containing DNA by Phage-modified RNA polymerase," *J. Mol. Biol.* 139(3): 407-422, May 25, 1980.

McLaughlin, J.R. et al., "Unique Features in the Ribosome Binding Site Sequence of the Gram-positive *Staphylococcus aureus* β-Lactamase Gene," *The Journal of Biological Chemistry* 256(21): 11283-11291, Nov. 10, 1981.

Michel, B. et al., "DNA cloning in *Bacillus subtilis*. III. Efficiency of random-segment cloning and insertional inactivation vectors," *Gene* 12: 147-154, 1980.

(Continued)

*Primary Examiner*—Maria Marvich
(74) *Attorney, Agent, or Firm*—Seed IP Law Group PLLC

(57) ABSTRACT

Nucleic acid expression control sequence cassettes and vectors containing the same are provided for use in making abundant quantities of recombinant polypeptides of interest. The modified transcriptional control sequences, which include a T5 promoter sequence, are highly stable and can be used in a variety of vectors, such as plasmids.

21 Claims, 8 Drawing Sheets

OTHER PUBLICATIONS

Moran, C.P. et al., "Nucleotide sequence of *Bacillus subtilis* promoter recognized by *Bacillus subtilis* RNA polymerase containing $\sigma^{37}$," *Nucleic Acids Research* 9(22): 5979-5990, 1981.

Moran, C.P. et al., "Nucleotide Sequences that Signal the Initiation of Transcription and Translation in *Bacillus subtilis*," *Molec. gen. Genet.* 186(3): 339-346, 1982.

Moran, C.P. et al., "Promoter for a Developmentally Regulated Gene in *Bacillus subtilis*," *Cell* 25(3): 783-791, Sep. 1981.

Murray, C.L. et al., "Nucleotide Sequences of Transcription and Translation Initiation Regions in *Bacillus* Phage φ29 Early Genes," *The Journal of Biological Chemistry* 257(2): 1053-1062, Jan. 25, 1982.

NCBI sequence viewer, J01636, *E. coli* lactose operator sequence, date available May 5, 1993, NCBI, pp. 1-10 accessed on Nov. 8, 2004.

Novagen Catalog, pET-24a-d(+) Vector, TB070, Dec. 1998.

Nunberg, J.H. et al., "Structure and Genomic Organization of the Mouse Dihydrofolate Reductase Gene," *Cell* 19(2): 355-364, Feb. 1980.

Rosenberg, M. et al., "Determination of nucleotide sequences beyond the sites of transcriptional termination," *Proc. Natl. Acad. Sci. USA* 73(3)(: 717-721, Mar. 1976.

Schoner, R. et al., "Enhanced expression of mouse dihydrofolate reductase in *Bacillus subtilis*," *Gene* 22: 47-57, 1983.

Simons, G. et al., "High-level expression of human interferon gamma in *Escherichia coli* under control of the $\rho_L$ promoter of bacteriophage lambda," *Gene* 28: 55-64, 1984.

Stüber, D. et al., "Electron Microscopic Analysis of in vitro Transcriptional Complexes: Mapping of Promoters of the Coliphage T5 Genome," *Molec. gen. Genet.* 166(2): 141-149, 1978.

Stüber, D. et al., "Organization to transcriptional signals in plasmids pBR322 and pACYC184," *Proc. Natl. Acad. Sci. USA* 78(1): 167-171, Jan. 1981.

Stueber, D. et al., "A novel in vitro transcription-translation system: accurate and efficient synthesis of single proteins from cloned DNA sequences," *The EMBO Journal* 3(13): 3143-3148, Dec. 1984.

von Gabain, A. et al., "Interaction of *Escherichia coli* RNA polymerase with promoters of several coliphage and plasmid DNAs," *Proc. Natl. Acad. Sci. USA* 76(1): 189-193, Jan. 1979.

West, R.W. et al., "Construction and Characterization of *E. coli* Promoter-Probe Plasmid Vectors. II. RNA Polymerase Binding Studies on Antibiotic-Resistance Promoters," *Gene* 9(3/4): 175-193, May 1980.

Zukowski, M.M. et al., "Chromogenic identification of genetic regulatory signals in *Bacillus subtilis* based on expression of a cloned *Pseudomonas* gene," *Proc. Natl. Acad.Sci. USA* 80(4): 1101-1105, Feb. 1983.

Frank et al., "Thermodynamics of the Interactions of Lac Repressor with Variants of the Symmetric Lac Operator: Effects of Converting a Consensus Site to a Non-specific Site," J. Mol. Biol., 267:1186-1206, 1997.

Simons et al., "Possible ideal lac operator: *Escherichia coli* lac operator-like sequences from eukaryotic genomes lack the central G C pair," Proc. Natl. Acad. Sci. USA, 81:1624-1628, Mar. 1984.

```
              P_T5
BglII      ┌ -35    Operator I    -10 ┐    Operator II
5'-AGATCTAAATCATAAAAAATTTATTTGCTTTGTGAGCGGATAACAATTATAATAGATTCAATTGTGAGCGGATAACAATTTCA
   TCTAGATTTAGTATTTTTTAAATAAACGAAACACTCGCCTATTGTTAATATTATCTAAGTTAACACTCGCCTATTGTTAAAGT EcoRI      RBS         NdeI
CACAGAATTCATTAAAGAGGAGAAATTACATATGAATCCATCACCTAGAAAACGC-3'
GTGTCTTAAGTAATTTCTCCTCTTTAATGTATACTTAGGTAGTGGATCTTTTGCG
```

*Fig. 3A*

```
  BglII                -35     lac operator I   -10      lac
3'-AGATCTAAATCATAAAAAATTTATTTGCTTTGTGAGCGGATAACAATTATAATAGATTCAATTGT operator II      EcoRI       RBS        NdeI
GAGCGGATAACAATTTCACACAGAATTCATTAAAGAGGAGAAATTACATATG-5'
```

*Fig. 3B*

BglQE-F primer ⎯⎯⎯⎯⎯⎯⎯⎯⎯⎯⎯▶
  GAAGATCTAAATCATAAAAAATTTATTTGC                                                    T5PRO1F primer
5'-AGATCTAAATCATAAAAAATTTATTTGCTTTGTGAGCGGATAACAATTATAATAGATTCAATTcTaAatttAcAAgAATTT
   TCTAGATTTAGTATTTTTTAAATAAACGAAACACTCGCCTATTGTTAATATTATCTAAGTTAAgAtTtaaaTgTTcTTAAA
                                                            T5PRO1R primer CACACAGAATTCATTAAAGAGGAGAAATTACATATGAATCCATCACCTAGAAAACGC-3'
GTGTGTCTTAAGTAATTTCTCCTCTTTAATGTATACTTAGGTAGTGGATCTTTTGCG
                  CTCCTCTTTAATGTATACTTAGGTAGTGGATCT
                  ◀⎯⎯⎯⎯⎯⎯⎯NdeQE-R primer

*Fig. 3C*

-35                        -10
5'-AGATCTAAATCATAAAAAATTTATTTGCTTTGTGAGCGGATAACAATTATAATAGATTCAATTGTGAGCGGATAACAATTATA
   TCTAGATTTAGTATTTTTTAAATAAACGAAACACTCGCCTATTGTTAATATTATCTAAGTTAACACTCGCCTATTGTTAATAT
                                                                      T5PRO1R primer
             T5PRO1F primer
ATAGATTCAATTcTaAatttAcAAgAATTTCACACAGAATTCATTAAAGAGGAGAAATTACATATGAATCCATCACCTAGAAAACGC-3'
TATCTAAGTTAAgAtTtaaaTgTTcTTAAAGTGTGTCTTAAGTAATTTCTCCTCTTTAATGTATACTTAGGTAGTGGATCTTTTGCG
                                       CTCCTCTTTAATGTATACTTAGGTAGTGGATCT
                                       ◀⎯⎯⎯⎯⎯⎯⎯NdeQE-R primer

*Fig. 3D*

EFFICIENT PROTEIN EXPRESSION SYSTEM

CROSS-REFERENCE TO RELATED APPLICATIONS

This application is a continuation of U.S. patent application Ser. No. 10/284,083 filed Oct. 28, 2002, now issued as U.S. Pat. No. 6,939,959 on Sep. 6, 2005, which claims the benefit of U.S. Provisional Patent Application No. 60/348,434 filed Oct. 26, 2001, which applications are incorporated herein by reference in their entireties.

BACKGROUND OF THE INVENTION

1. Field of the Invention

The present invention relates generally to the nucleic acid expression systems, and more specifically, to nucleic acid expression control sequence cassettes comprising a stable bacteriophage T5 promoter and nucleic acid regulatory sequences useful for generating efficient and stable expression vectors for high-level protein expression.

2. Description of the Related Art

A demand for the efficient production of biologics for therapeutic use is steadily increasing as more products, such as recombinant proteins, are approved or are nearing approval for use in humans. Bacterial fermentation processes have long been, and still are, the major tool for production of these types of molecules. The key objective of process optimization is to attain a high yield of product having the required quality at the lowest possible cost, which is often determined by the properties of a specific expression construct or system. For example, high-level recombinant protein expression may overwhelm the metabolic capacity of a host cell, which often impairs efficient protein production.

Hence, a need exists for identifying and developing additional nucleic acid expression systems useful for the efficient and stable production of therapeutically effective agents. The present invention meets such needs, and further provides other related advantages.

BRIEF SUMMARY OF THE INVENTION

The present invention provides the discovery of a stable nucleic acid expression control sequence for high-level expression of recombinant proteins.

In one aspect, the invention provides a nucleic acid expression control sequence cassette, comprising (a) a transcription initiation sequence capable of remaining hybridized under stringent conditions to a T5 promoter sequence, wherein said transcription initiation sequence has at least basal T5 promoter transcriptional activity; (b) at least one regulatory sequence operably linked to said transcription sequence of (a) and capable of remaining hybridized under stringent conditions to a lac operator sequence, wherein said at least one regulatory sequence specifically binds a lacI repressor protein and thereby alters transcriptional activity; (c) at least one mutated regulatory sequence of (b) wherein said at least one mutated regulatory sequence does not specifically bind a lacI repressor protein and thereby does not alter transcriptional activity; and (d) a translation initiation sequence. In another embodiment, (c) is a cis-acting nucleotide sequence or transcriptional spacer comprising up to about 30 nucleotides. In another embodiment, the aforementioned cassettes further comprise at least one restriction enzyme recognition site at about the 3'-end and at least one restriction enzyme recognition site at about the 5'-end. In a related embodiment, the at least one restriction enzyme recognition site at about the 5'-end is Bg/II and said at least one restriction enzyme recognition site at about the 3'-end is NdeI. In a further embodiment, any of the aforementioned cassettes comprise SEQ ID NO:2 or 3.

In another aspect, the present invention provides a nucleic acid expression vector comprising any of the aforementioned nucleic acid expression control sequence cassette. In certain embodiments, the expression vector may be a plasmid, a cosmid, a shuttle vector, a viral vector, an insect vector, and a YAC, preferably a plasmid. In a particular embodiment, the expression vector is pT5 (SEQ ID NO:1). In other embodiments, the expression vector has the any of the aforementioned cassettes operably linked to at least one nucleic acid coding sequence. In related embodiments, the nucleic acid coding sequences encode a polypeptide selected from a bacteriophage polypeptide, a bacterial polypeptide, a fungal polypeptide, a viral polypeptide, an insect polypeptide, a plant polypeptide, or a mammalian polypeptide. In still other embodiments, there is provided any of the aforementioned expression vectors wherein said at least one nucleic acid coding sequence encodes an immunogenic hybrid polypeptide comprising at least one bacterial polypeptide, preferably said immunogenic hybrid polypeptide comprises a hybrid multivalent group A streptococcal M polypeptide or a hybrid polypeptide of *Yersinia pestis* polypeptides F1 and V.

In a further aspect, the invention provides a method for producing one or more polypeptide(s), comprising (a) culturing a cell containing the expression vector of claim 9 under conditions sufficient to express one or more polypeptide(s); and (b) isolating said polypeptide(s). In one embodiment, the aforementioned method wherein said expressed polypeptide is selected from a bacteriophage polypeptide, a bacterial polypeptide, a fungal polypeptide, a viral polypeptide, an insect polypeptide, a plant polypeptide, or a mammalian polypeptide. In other embodiments, said cell is selected from the group consisting of a bacterium, a fungus, an insect cell, a plant cell, and a mammalian cell, preferably a bacterium. In certain embodiments, the aforementioned methods provide expressed polypeptide(s) in soluble form. In one embodiment, any of the aforementioned methods provide expressed polypeptides comprising a hybrid multivalent group A streptococcal M polypeptide or a hybrid polypeptide of *Yersinia pestis* polypeptides F1 and V. In another related embodiment, any of the aforementioned methods wherein the expression vector is pT5 (SEQ ID NO:1).

BRIEF DESCRIPTION OF THE DRAWINGS

FIGS. 3A to 3D show the nucleic acid sequence of various expression control sequences. FIG. 3A shows the T5 promoter/lac operator expression control sequence (SEQ ID NO:4) found in the pQE-40 plasmid (Qiagen, Valencia, Calif.). FIG. 3B shows the portion of the T5 promoter/lac operator in pQE-40 that appears to be unstable and is often deleted (boxed sequence) when cloned (SEQ ID NO:11). FIGS. 3C and 3D show two embodiments wherein the T5 promoter/lac operator region is modified and surprisingly rendered stable (SEQ ID NOS:5 and 6). Lower case, bold letters in FIGS. 3C and 3D identify the mutated lacO nucleotides (8 of 19 total), and boxed in FIG. 3D is the 32 base pair insertion that includes a mutated lacO.

DETAILED DESCRIPTION OF THE INVENTION

Figure 1:
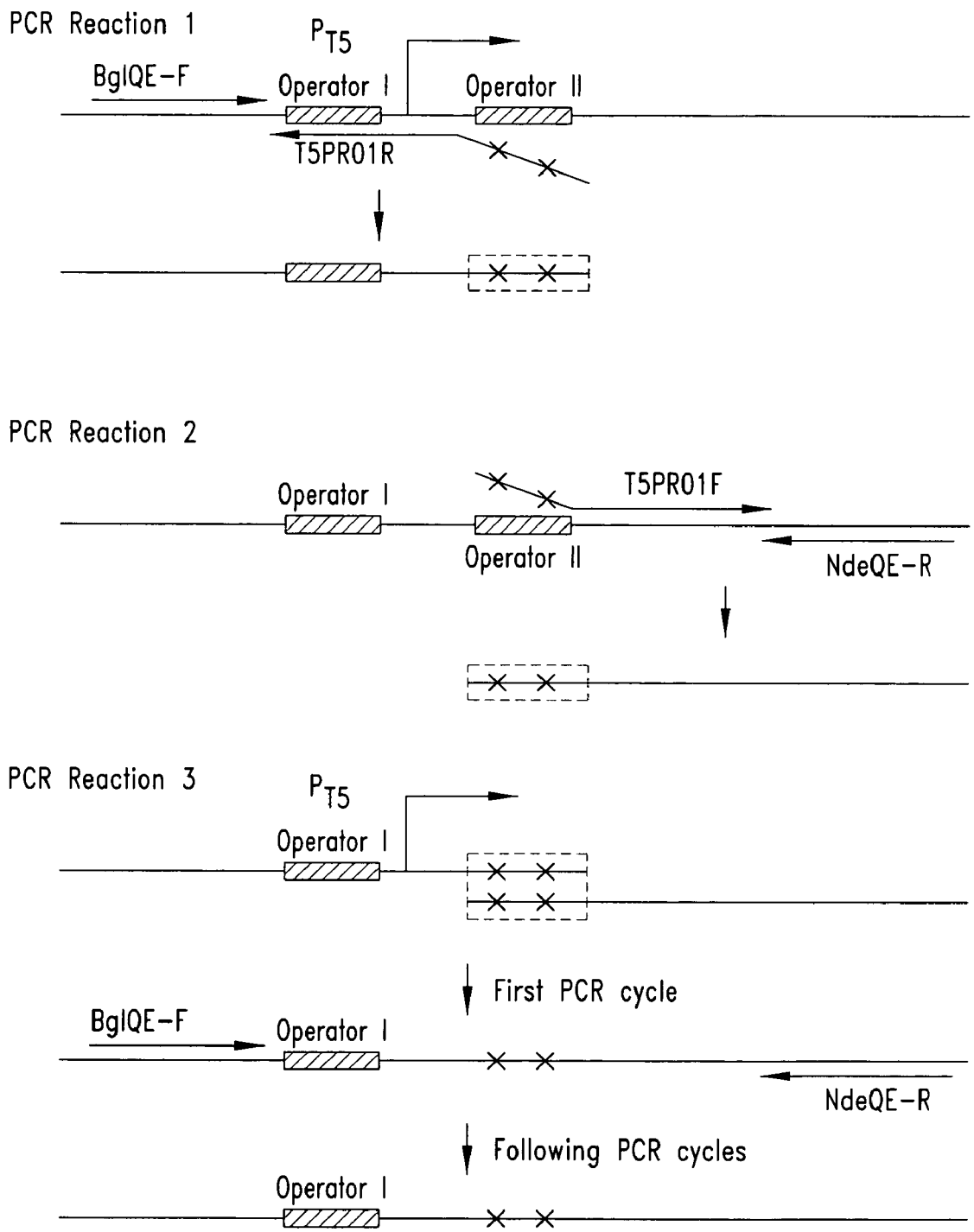
FIG. 1 shows a schematic diagram of the process for making one embodiment of a modified T5 promoter and lac operator using PCR. This series of reactions results in a T5 promoter operably linked to at least one functional lac operator followed by a mutated lac operator (that can no longer function as an operator). Primers BglQE-F (SEQ ID NO:7) and T5PRO1R (SEQ ID NO:10) were used in the first PCR reaction (wherein T5PRO1R primes at operator 1), primers NdeQE-R (SEQ ID NO:8) and T5PRO1F (SEQ ID NO:9) were used in the second PCR reaction, and finally primers BglQE-F and NdeQE-R were used to generate SEQ ID NO:3.

As noted above, the present invention is generally directed to nucleic acid expression control sequence cassettes, which can be used to generate nucleic acid expression vectors. When introduced to the proper host cell, these expression vectors will stably and efficiently produce a variety of recombinant polypeptides. Furthermore, the cassettes may be introduced into a variety of different vector backbones (such as plasmids, cosmids, viral vectors, and the like) so that recombinant protein expression can be accomplished in a variety of different host cells (such as bacteria, yeast, mammalian cells, and the like). The present invention is also directed to methods of producing and isolating recombinant proteins using the nucleic acid expression control sequence cassettes operably linked to a nucleic acid coding sequence. For example, without limitation, the nucleic acid expression control sequence cassettes of this invention can be used to produce immunogenic polypeptides, such as a hybrid group A streptococcal polypeptides or plague fusion proteins.

By way of background, and not wishing to be bound by theory, the level of recombinant protein production from a nucleic acid expression vector is influenced by a variety of factors, including without limitation, the copy number of the vector, the strength of the promoter, the activity and localization of the recombinant protein being expressed, the host cell being used, alignment of the codon usage in the recombinant protein and host cell, and how efficiently the promoter is regulated. For example, the pQE expression plasmids (QIAGEN, Valencia, CA) contain an inducible expression element consisting of phage T5 promoter and two lac operator sequences (lacO). *E. coli* RNA polymerase recognizes the bacteriophage T5 promoter, which is transcribed at a very high rate. Two lacO sequences are included in the pQE plasmids to presumably allow more Lac repressor protein (lacI) binding to ensure efficient repression of the powerful T5 promoter. In addition, the extremely high transcription rate initiated at the T5 promoter can only be efficiently regulated and repressed by the presence of high levels of lacI. Hence, to provide high levels of lacI, the pQE vectors are typically introduced into *E. coli* host strains carrying the low-copy plasmid pREP4, which constitutively expresses lacI (has the high expressing lacI$^q$ mutant). Any *E. coli* host strain containing both the expression plasmid (pQE) and the repressor (pREP4) plasmid can be used for the controlled production of recombinant proteins. Recently, a cis-repressed pQE have the coding sequence for lacI repressor contained directly on the pQE plasmid was generated (e.g., see pQE80L; see Internet at qiagen.[dot]com).

Although a strong, but regulated, promoter may be desirable to more easily produce abundant amounts of a recombinant protein, some proteins may be toxic for a host cell even when small amounts are produced due to "leakage" of the promoter (i.e., when a negatively regulated promoter still produces some protein). Therefore, strong suppression of recombinant protein expression may be desirable. In other instances, a nucleic acid expression vector may be unstable and, for reasons unknown, a host will cause the coding sequence for a recombinant protein to be recombinantly removed from the vector. By way of example, the expression of recombinant *Thermus thermophilus* ribonuclease H that had been cloned into pQE-40 (pQE-rnhA) was found to be very unstable in *E. coli*. The rnhA was removed from the pQE-40 plasmid and cloned into the pET-24a vector (Novagen, Madison, Wis.). The resultant plasmid, pET-24a-rnhA, proved to be highly stable and provided high-level protein expression in the BL21 (DE3) *E. coli* host cells (Novagen).

Therefore, the T7/lac operator expression control sequence between the BgI/II and NdeI sites was then replaced with a T5 promoter/lac operator expression control sequence that was generated by PCR (see FIG. 3A), to create plasmid pET-T5-rnhA. However, the new construct showed no expression of the ribonuclease H enzyme. Upon sequencing, it was discovered that a 32 base pair fragment of the T5 promoter/lac operator expression control sequence was deleted in pET-T5-rnhA (see FIG. 3B, box identifies the deletion). Part of the deletion included the −10 TATA box portion of the T5 promoter, which explained why no expression of the recombinant rnhA gene was occurring. By way of background, and not wishing to be bound by theory, it appears that the original T5 promoter/lac operator expression control sequence was unstable because the duplicated lac operator sequences may have been involved in recombination events that deleted a 32 base pair fragment from pET-T5-rnhA. Thus, to solve this problem, site-directed mutagenesis by PCR was performed to generate a modified T5 promoter/lac operator expression control sequence cassette, which was stable.

The invention, therefore, relates generally to the surprising discovery, as provided in the present disclosure, that modification of the nucleotide sequence within a T5 promoter/lac operator expression control sequence provides a stable promoter/operator: region that results in consistent and high-level expression of recombinant proteins in host cells, and a nucleic acid expression control sequence that can be flanked by, for example, restriction endonuclease sites for isolation and cloning into any desired vector. Moreover, the modified nucleic acid expression control sequence may include one or more mutations, which can include a substitution, a deletion, an insertion, and a combination thereof. Preferably, a modified nucleic acid expression control sequence of the present invention has a substitution mutation, more preferably an insertion mutation, and most preferably a combination of a substitution mutation and insertion mutation. In a preferred embodiment, the present invention provides a nucleic acid expression control sequence cassette comprising (a) a transcription initiation sequence capable of remaining hybridized under stringent conditions to a T5 promoter sequence, wherein said transcription initiation sequence has at least basal T5 promoter transcriptional activity; (b) at least one regulatory sequence operably linked to said transcription sequence of (a) and capable of remaining hybridized under stringent conditions to a lac operator sequence, wherein said at least one regulatory sequence specifically binds a lacI repressor protein and thereby alters transcriptional activity; (c) at least one mutated regulatory sequence of (b) wherein said at least one mutated regulatory sequence does not specifically bind a lacI repressor protein and thereby does not alter transcriptional activity; and (d) a translation initiation sequence.

A similar expression system relates to the T7 promoter (see U.S. Pat. Nos. 4,952,496, 5,693,489, and 5,869,320), except that the T7 promoter requires a specific T7 RNA polymerase (in contrast, transcription from the T5 promoter can occur with a host RNA polymerase). The T7 RNA polymerase must be provided in bacterial host (typically as a bacteriophage lysogen) and, therefore, cloning of a polynucleotide coding sequence must first take place in a bacterial strain lacking the T7 RNA polymerase, and then expression requires transfer to a bacterial lysogen that makes the T7 RNA polymerase. One advantage of the nucleic acid expression control system of the present invention is that a single host cell can be used for both cloning of a polynucleotide coding sequence and for expression of the polypeptide encoded by a polynucleotide coding sequence. For example, any bacterial host cell that produces lacI repressor protein (preferably a lacI expressed from the lacI$^q$ gene) can be used to introduce a nucleic acid expression control sequence of the present invention carried on a vector, such as a plasmid. In addition, any nucleic acid expression control sequence of the present invention can be used, as described herein, with a vector that also carries the lacI$^q$ gene and is capable of replicating in a bacterial host (e.g., pT5, SEQ ID NO:1).

Moreover, the transcription initiation sequence is preferably capable of remaining hybridized under stringent conditions to a T5 promoter sequence, wherein said transcription initiation sequence has at least basal T5 promoter transcriptional activity. Thus, a variety of T5 promoter sequences may be used, including without limitation those described in U.S. Pat. Nos. 4,495,280 and 4,868,111. As used herein, "basal activity" means that transcription is detectable by methods known in the art. The surprising result of the present invention is insertion of a non-coding cis-acting nucleic acid sequence, which functions as a transcribed spacer sequence, stabilizes the T5 promoter/lac operator portion of the nucleic acid expression control sequence. In one preferred embodiment, an insertion downstream of the transcription initiation sequence and at least one regulatory sequence comprises a cis-acting nucleotide sequence or a transcribed spacer comprising up to 32 nucleotides.

"Nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Preferably, the nucleic acids of the present invention are produced by PCR. Nucleic acids may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety may be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids" (PNAs), which comprise naturally occurring or modified nucleic acid bases attached to a polyamide backbone. Nucleic acids can be either single stranded or double stranded.

Further, an "isolated nucleic acid molecule" refers to a polynucleotide molecule in the form of a separate fragment or as a component of a larger nucleic acid construct, which has been separated from its source cell (including the chromosome it normally resides in) at least once in a substantially pure form. For example, a DNA molecule that encodes a recombinant polypeptide, peptide, or variant thereof, which has been separated from a cell or from the genomic DNA of a cell, is an isolated DNA molecule. Another example of an isolated nucleic acid molecule is a bacteriophage promoter (e.g., T5 or T7), or nucleic acid expression control sequence cassette of the present invention, cloned into a plasmid capable of replication in a bacterial host cell. Still another example of an isolated nucleic acid molecule is a chemically synthesized nucleic acid molecule. Nucleic acid molecules may be comprised of a wide variety of nucleotides, including DNA, cDNA, RNA, nucleotide analogues, or some combination thereof. In certain preferred embodiments, an isolated nucleic acid molecule is an expression control sequence cassette comprising a nucleic acid sequence as set forth in SEQ ID NOS:1, 2, 3, 5, or 6. Preferably, the nucleic acid expression control sequence cassette is double stranded DNA.

Nucleic acid expression control sequences of this invention may be designed for inclusion within a nucleic acid sequence cassette. As used herein, a "sequence cassette" refers to a contiguous nucleic acid molecule that can be isolated as a single unit and cloned as a single unit. For example, a sequence cassette may be created enzymatically (e.g., by using type I or type II restriction endonucleases, exonucleases, etc.), by mechanical means (e.g., shearing), by chemical synthesis, or by recombinant methods (e.g., PCR). An advantage of the present invention is that a nucleic acid expression control sequence comprising (a) a transcription initiation sequence capable of remaining hybridized under stringent conditions to a T5 promoter sequence, wherein said transcription initiation sequence has at least basal T5 promoter transcriptional activity; (b) at least one regulatory sequence operably linked to said transcription sequence of (a) and capable of remaining hybridized under stringent conditions to a lac operator sequence, wherein said at least one regulatory sequence specifically binds a lacI repressor protein and thereby alters transcriptional activity; (c) at least one mutated regulatory sequence of (b) wherein said at least one mutated regulatory sequence does not specifically bind a lacI repressor protein and thereby does not alter transcriptional activity; and (d) a translation initiation sequence, may be constructed by, for example, PCR as a sequence cassette that is flanked by restriction endonuclease sites.

Any preferred restriction endonuclease site may be incorporated (see list of at least 215 commercially available restriction endonucleases in the New England Biolabs 2002 catalog, which is hereby incorporated by reference). Preferably, the nucleic acid expression control sequence cassette comprises at least one restriction enzyme recognition site at about the 3'-end and at least one restriction enzyme recognition site at about the 5'-end. More preferably, the restriction enzyme recognition site of the nucleic acid expression control sequence cassette at about the 5'-end is Bg/II and the restriction enzyme recognition site at about the 3'-end is NdeI. Preferably, the nucleic acid expression control sequence cassette with the restriction enzyme sites at the 3'- and 5'-ends comprises SEQ ID NOS:2 or 3.

As used herein, the term "about" or "consists essentially of" refers to ±10% within a recited position or of any indicated structure, value, or range. In addition, any numerical ranges recited herein are to be understood to include any integer within that range and, where applicable (e.g., concentrations), fractions thereof, such as one tenth and one hundredth of an integer (unless otherwise indicated).

Preferred nucleic acid expression control sequences include at least one translation initiation sequence, which may be derived from many sources, to aid in producing a recombinant protein of interest. In one embodiment, the translation initiation sequence is a ribosome binding site (RBS) from the bacterial gene lacZ. Other translation initiation sequences or ribosome binding sites may be obtained from genes derived from mammalian coding sequences, fungal coding sequences, viral coding sequences, plant coding sequences, bacteriophage coding sequences, and the like.

In another aspect, the nucleic acid expression control sequences comprising a transcription initiation sequence capable of remaining hybridized under stringent conditions to a T5 promoter sequence, at least one regulatory sequence operably linked to the transcription sequence and capable of remaining hybridized under stringent conditions to a lac operator sequence, and a translation initiation sequence, also comprise a at least one mutated regulatory sequence wherein the mutated regulatory sequence no longer functions as such. For example, an exemplary lacO sequence comprised of 19 nucleotides may be mutated by substitution of 8 nucleotides, which can no longer specifically bind a lacI repressor protein and thereby can no longer alter transcriptional activity when operably linked to a transcription initiation sequence. Preferably, the mutated regulatory sequence also no longer remains hybridized under stringent conditions to a lac operator sequence. Alternatively, a nucleic acid sequence up to 150 nucleotides instead of a mutated regulatory sequence may be used, preferably inserted downstream (i.e., to the 3'-side) of the at least one regulatory sequence operably linked to the transcription initiation sequence.

In one preferred embodiment, the nucleic acid expression control sequence of this invention comprises at least one functional regulatory sequence operably linked to a transcriptional activation sequence and at least one substitution mutated regulatory sequence that is no longer capable of altering transcription (for illustrative purposes, see FIG. 3C). In a more preferred embodiment, the nucleic acid expression control sequence of this invention comprises at least two functional regulatory sequences operably linked to a transcriptional activation sequence and at least one insertion of a substitution mutated regulatory sequence that is no longer capable of altering transcription (for illustrative purposes, see FIG. 3D). Therefore, a T5 promoter/lac operator expression control sequence is surprisingly stabilized by an insertion of a nucleic acid sequence that is non-regulatory and is up to about 150 nucleotides in length, preferably is about 10 to about 50 nucleotides, more preferably is about 20 nucleotides to about 40 nucleotides, and most preferably is about 25 to about 35 nucleotides in length. In one preferred embodiment, the insertion is a cis-acting nucleotide sequence or a transcribed spacer consisting essentially of 32 nucleotides.

In certain aspects, the invention relates to nucleic acid vectors and constructs that include nucleic acid expression control sequence cassettes of the present invention, and in particular to "nucleic acid expression constructs" that include any nucleic acid expression control sequence cassette as provided herein. In addition, the nucleic acid expression constructs may further comprise a nucleic acid expression control sequence of the present invention operably linked to one or more polynucleotide coding sequences. Also provided by the present invention are nucleic acid expression constructs, and host cells containing such nucleic acids that encode recombinant polypeptides and variants thereof. In certain embodiments, the nucleic acid coding sequences may encode a polypeptide selected from a bacteriophage polypeptide, a bacterial polypeptide, a fungal polypeptide, a viral polypeptide, an insect polypeptide, a plant polypeptide, or a mammalian polypeptide.

For example, the nucleic acid expression constructs of the present invention can be used to express recombinant polypeptides capable of eliciting an immune response against one or more antigens, such as the group A streptococci M proteins or plague virulence proteins F1 and V. One aspect of the invention pertains to isolated nucleic sequences encoding a hybrid polypeptide sequence as described herein, as well as those sequences readily derived from isolated nucleic acid molecules such as, for example, complementary sequences, reverse sequences and complements of reverse sequences.

Appropriate cloning and expression vectors for use with prokaryotic and eukaryotic hosts are described, for example, by Sambrook et al., *Molecular Cloning: A Laboratory Manual*, Second Edition, Cold Spring Harbor, N.Y., (1989), and may include plasmids, cosmids, shuttle vectors, viral vectors and vectors comprising a chromosomal origin of replication as disclosed therein (e.g., yeast artificial chromosome or YAC). Generally, nucleic acid expression vectors include origins of replication and selectable markers permitting detectable transformation of the host cell, e.g., the ampicillin resistance gene of *E. coli* and *S. cerevisiae* TRP1 gene, and an expression control sequence such as a promoter. For purposes of the present invention, the nucleic acid expression control sequence cassettes of this invention may be used to replace an expression control sequence already existing in a particular desired vector. In addition, a heterologous structural sequence may be included in appropriate phase with translation initiation sequences and termination sequences of the vector. Optionally, a heterologous sequence can encode a fusion protein including an amino-terminal (or a carboxy-terminal) identification peptide imparting desired characteristics, e.g., stabilization or simplified purification of expressed recombinant product. In particularly preferred embodiments, for example, recombinant polypeptides are fused in-frame to a carboxy-terminal tag, which tag may be any one of alkaline phosphatase, β-galactosidase, hexahistidine (6×His), FLAG® epitope tag (DYKDDDDK, SEQ ID NO:12), or GST, and the like. Most preferred are recombinant fusion proteins that facilitate affinity detection and isolation of the hybrid polypeptides and may include, for example, poly-His or the defined antigenic peptide epitopes described in U.S. Pat. No. 5,011,912 and in Hopp et al., (1988 *Bio/Technology* 6:1204), or the XPRESS™ epitope tag (DLYDDDDK, SEQ ID NO:13; Invitrogen, Carlsbad, Calif.). The affinity sequence may be a hexa-histidine tag as supplied by a vector, such as, for example, pBAD/His (Invitrogen). Alternatively, the affinity sequence may be added either synthetically or engineered into the primers used to recombinantly generate the nucleic acid coding sequence (e.g., using the polymerase chain reaction). Preferably, a recombinant polypeptide is fused to a polyhistidine and is encoded by a recombinant nucleic acid sequence encoding such a fusion protein.

Expression constructs for bacterial use may be constructed by inserting into an expression vector a structural DNA sequence encoding a desired protein together with a nucleic acid expression control sequence as described herein. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera *Pseudomonas, Streptomyces,* and *Staphylococcus*, although others may also be employed as a matter of choice. Any other plasmid or vector may be used as long as they are replicable and viable in the host.

As a representative but non-limiting example, expression vectors for bacterial use can comprise a selectable marker and a bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden), pGEM1 (Promega Corp., Madison, Wis., USA), and the T7 pET vectors (Novagen, Madison, Wis., USA). These pBR322 "backbone" sections may be combined with an appropriate nucleic acid expression control sequence of this invention and the structural sequence to be expressed. The pBR322 replication origin is considered medium copy, as is the replication origin of pACYC-based vectors, in that bacteria produce about 20-80 copies of the plasmid per cell. Low-copy vectors (less than 10 copies per cell), such as those based on pSC101, may also be used. High copy vectors, such those based on the pUC plasmids, may also be used. Preferably, the nucleic acid expression control sequence of the present invention is contained in low copy vector, a medium copy vector, or a high copy vector, and most preferably in a high copy vector.

Other vectors and constructs include chromosomal, non-chromosomal and synthetic DNA sequences, e.g., derivatives of SV40; bacterial plasmids; phage DNA; baculovirus; yeast plasmids; yeast artificial chromosomes (YACs); vectors derived from combinations of plasmids and phage DNA; shuttle vectors derived from combinations of plasmids and viral DNA; viral DNA, such as vaccinia, adenovirus, fowl pox virus, and pseudorabies. However, any other vector may be used for preparation of a nucleic acid expression construct as long as it is replicable and viable in the host cell of interest. Further, in some preferred embodiments, nucleic acid expression constructs containing the nucleic acid expression control sequence operably linked to polynucleotide coding sequence(s) for polypeptide(s) and fusion protein(s) may remain extrachromosomal, and in another preferred embodiments the expression constructs may integrate into at least one host cell chromosome.

In another preferred embodiment, the nucleic acid expression construct has a second expression control sequence such as a promoter, which may be lac, lacUV5, tac, trc, ara, trp, λ phage, T3 phage promoter, and T7 phage promoter, and more preferably is a T7 phage promoter. The "expression control sequence" refers to any sequences sufficient to allow expression of a protein of interest in a host cell, including one or more promoter sequences, enhancer sequences, operator sequences (e.g., lacO), and the like. In a preferred embodiment, the nucleic acid expression control sequence cassette is in a plasmid and the host cell is a bacterium. More preferably the plasmid is pT5 (SEQ ID NO:1) and the host cell is *Escherichia coli*. In certain preferred embodiments the second expression control sequence is an "externally regulated promoter," which includes functional promoter sequences having activity that may be altered (e.g., increased or decreased) by an additional element, agent, molecule, component, co-factor or the like. An externally regulated promoter may comprise, for example, a repressor binding site, an activator binding site or any other regulatory sequence that controls expression of a polynucleotide sequence as provided herein. In certain particularly preferred embodiments, the externally regulated promoter is a tightly regulated promoter that is specifically inducible and that permits little or no transcription of polynucleotide sequences under its control in the absence of an induction signal, as is known to those familiar with the art and described, for example, in Guzman et al. (*J. Bacteriol.*, 1995, 177:4121), Carra et al. (*EMBO J.*, 1993, 12:35), Mayer (*Gene,* 1995, 163:41), Haldimann et al. (*J. Bacteriol.*, 1998, 180:1277), Lutz et al. (*Nucleic Acids Res.*, 1997, 25:1203), Allgood et al. (*Curr. Opin. Biotechnol.*, 1997, 8:474) and Makrides (*Microbiol. Rev.*, 1996, 60:512). In other preferred embodiments of the invention, a second externally regulated promoter is present that is inducible but that may not be tightly regulated. In certain other preferred embodiments a second promoter is present in the expression construct of the invention that is not a regulated promoter; such a promoter may include, for example, a constitutive promoter such as an insect polyhedrin promoter or a yeast phosphoglycerate kinase promoter (see, e.g., Giraud et al., 1998 *J. Mol. Biol.* 281:409). A nucleic acid expression construct may also contain a transcription terminator. A vector may also include appropriate sequences for amplifying expression.

Transcription of a DNA sequence encoding a polypeptide by higher eukaryotes may be increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

As noted above, in certain embodiments the vector may be a viral vector such as a retroviral vector. For example, retroviruses from which a retroviral plasmid vector may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

While particular embodiments of nucleic acid expression control sequences are depicted in SEQ ID NOS:1, 2, 3, 5, and 6, within the context of the present invention, reference to one or more isolated nucleic acids includes variants of these sequences that are substantially similar in that they are structurally similar and remain capable of functioning as expression control sequences by being specific for one or more regulatory proteins. As used herein, the nucleotide sequence is deemed to be "substantially similar" if: (a) the nucleotide sequence is derived from a transcription initiation sequence or a regulatory sequence and retain the ability to initiate transcription or alter the level of transcription, respectively; (b) the nucleotide sequence is capable of hybridization to the nucleotide sequences of the present invention under stringent conditions; or (c) is a complement of any of the sequences described in (a) and (b).

"Specific for" refers to the ability of a protein (e.g., repressor, inducer) to selectively bind a nucleic acid regulatory sequence and/or an expression regulatory protein. Association or "binding" of a regulator protein to a specific nucleic acid or protein generally involve electrostatic interactions, hydrogen bonding, Van der Waals interactions, and hydrophobic interactions. Any one of these or any combination thereof can play a role in the binding between a regulatory protein and its ligand. Such a regulatory protein (e.g., lacI) generally associates with a specific nucleic acid sequence (e.g., lacO) with an dissociation constant ($K_d$) of at least $10^{-8}$ M, preferably at least $10^{-9}$ M, more preferably at least $10^{-10}$ M, still more preferably at least $10^{-11}$ M and most preferably at least $10^{-12}$ M. Affinity and dissociation constants may be determined by one of ordinary skill in the art using well-known techniques (see Scatchard, *Ann. N.Y. Acad. Sci.* 51:660-672, 1949).

As used herein, two nucleotide sequences are said to "hybridize" or "remain hybridized" under conditions of a specified stringency when stable hybrids are formed between substantially complementary nucleic acid sequences. Stringency of hybridization refers to a description of the environment under which hybrids are annealed and washed, which typically includes ionic strength and temperature. Other factors that might affect hybridization include the probe size and the length of time the hybrids are allowed to form. For example, "high," "medium" and "low" stringency encompass the following conditions or equivalent conditions thereto: high stringency is 0.1×SSPE or SSC, 0.1% SDS, 65° C.; medium stringency is 0.2×SSPE or SSC, 0.1% SDS, 50° C.; and low stringency is 1.0×SSPE or SSC, 0.1% SDS, 50° C. As used herein, the term "high stringency conditions" means that one or more sequences will remain hybridized only if there is at least 95%, and preferably at least 97%, identity between the sequences. In preferred embodiments, the nucleic acid expression control sequences of this invention comprise a transcription initiation sequence capable of remaining hybridized under stringent conditions to a T5 promoter sequence, which includes transcription initiation sequences that have at least basal T5 promoter transcriptional activity. In another preferred embodiment, the nucleic acid expression control sequence of this invention comprise a regulatory sequence capable of remaining hybridized under stringent conditions to a lac operator sequence, which includes regulatory sequences that specifically bind a lacI repressor protein and thereby can alter transcriptional activity when operably linked to a transcription initiation sequence.

It should be further understood that recombinant polypeptide-encoding nucleic acids could include variants of the natural sequence due to, for example, the degeneracy of the genetic code (including alleles). Briefly, such "variants" may result from natural polymorphisms or may be synthesized by recombinant methodology (e.g., to obtain codon optimization for expression in a particular host) or chemical synthesis, and may differ from wild-type polypeptides by one or more amino acid substitutions, insertions, deletions, or the like. Variants encompassing conservative amino acid substitutions include, for example, substitutions of one aliphatic amino acid for another, such as Ile, Val, Leu, or Ala or substitutions of one polar residue for another, such as between Lys and Arg, Glu and Asp, or Gln and Asn. Such substitutions are well known in the art to provide variants having similar physical properties and functional activities, such as for example, the ability to elicit and cross-react with similar antibodies. Other variants include nucleic acids sequences that encode a hybrid polypeptide having at least 50%, 60%, 70%, 80%, 90% or 95% amino acid identity to polynucleotide encoded recombinant proteins. Preferred embodiments are those having greater than 90% or 95% identity with the amino acid sequence to the polynucleotide encoded recombinant proteins.

As will be appreciated by those of ordinary skill in the art, a nucleotide sequence encoding a recombinant polypeptide or variant thereof may differ from the native sequence due to codon degeneracy, nucleotide polymorphism, or nucleotide substitution, deletion or insertion. Thus, in certain aspects the present invention includes all degenerate nucleic acid molecules that encode peptides, polypeptides, and proteins expressed using the nucleic acid expression control sequence of the present invention. In another aspect, included are nucleic acid molecules that encode recombinant polypeptide variants having conservative amino acid substitutions or deletions or substitutions such that the recombinant polypeptide variant retains at least one epitope capable of eliciting antibodies specific for the native protein.

In certain aspects, a nucleic acid sequence may be modified to encode a recombinant polypeptide variant wherein specific codons of the nucleic acid sequence have been changed to codons that are favored by a particular host and can result in enhanced levels of expression (see, e.g., Haas et al., *Curr. Biol.* 6:315, 1996; Yang et al., *Nucleic Acids Res.* 24:4592, 1996). For example, certain codons of the immunogenic peptides obtained from streptococcal M proteins (and expressed using pT5, SEQ ID NO:1) were optimized, without changing the primary sequence of the peptides, for improved expression in *Escherichia coli* (see FIG. 6). By way of illustration and not limitation, eleven of thirteen arginine (Arg) codons of AGG/AGA in the hexavalent A.1 hybrid polypeptide coding sequence were changed to the Arg codons of CGT/CGC in hexavalent A.3 coding sequence. As is known in the art, codons may be optimized for whichever host the hybrid polypeptide is to be expressed in, including without limitation bacteria, fungi, insect cells, plant cells, and mammalian cells. Additionally, codons encoding different amino acids may be changed as well, wherein one or more codons encoding different amino acids may be altered simultaneously as would best suit a particular host (e.g., codons for arginine, glycine, leucine, and serine may all be optimized or any combination thereof). Alternatively, codon optimization may result in one or more changes in the primary amino acid sequence, such as a conservative amino acid substitution, addition, deletion, or combination thereof.

Following transformation of a suitable host strain and growth of the host strain to an appropriate cell density, the nucleic acid expression control sequence, if it is an externally regulated promoter, is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well known to those skilled in the art.

A host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella tvphimurium*; fungal cells, such as yeast; insect cells, such as *Drosophila* S2 and *Spodoptera* Sf9; animal cells, such as MDCK, Hep-2, CHO or COS (e.g., COS-7); human cells such as Jurkat or 293 cells; adenoviruses; plant cells, or any suitable cell already adapted to in vitro propagation or so established de novo. The selection of an appropriate host is deemed to be within the scope of those skilled in the art from the teachings herein.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a nucleic acid expression control sequence of the present invention, optionally an enhancer, and also any necessary polyadenylation site, splice donor and acceptor sites, transcriptional termination sequences, and 5' flanking non-transcribed sequences. DNA sequences derived from the SV40 splice, and polyadenylation sites may be used to provide the required nontranscribed genetic elements.

Introduction of the construct into the host cell can be effected by a variety of methods with which those skilled in the art will be familiar, including but not limited to, for example, calcium phosphate transfection, liposome-mediated transfection, transfection with naked DNA, biolistic particle-mediated transfection, DEAE-Dextran mediated transfection, or electroporation. According to the present disclosure, and as will be appreciated by those having ordinary skill in the art, in certain embodiments at least one nucleic acid expression construct in a host cell may be extrachromosomal, while in certain embodiments at least one nucleic acid expression construct in a host cell may be integrated into a host cell chromosome.

In a preferred embodiment, this invention provides a method for producing one or more polypeptide(s) comprising culturing a cell containing an expression vector of the present invention under conditions permitting expression of one or more polypeptide(s) and isolating said polypeptide(s). Another preferred embodiment comprises a nucleic acid expression construct having an expression control sequence cassette operably linked to one polynucleotide coding sequence. The recombinant peptides, polypeptides, fusion proteins and the like may be expressed in mammalian cells, insect cells, plant cells, yeast or other fungi, bacteria, or other cells when part of an appropriate vector capable of replicating in one or more of such cells. Cell-free translation systems may also be employed to produce such proteins using RNAs derived from the nucleic acid expression constructs of the present invention.

One advantage of the nucleic acid expression control sequence of the present invention is that recombinant polypeptides may be overexpressed in soluble form. For example, a hybrid polypeptide of *Yersinia pestis* polypeptides F1 and V when overexpressed in a T7 expression system ends up in inclusion bodies, which fractionates into the insoluble fraction of whole cell lysates. Surprisingly, the same hybrid F1-V polypeptide contained in an expression vector and operably linked to a nucleic acid expression control sequence comprising (a) a transcription initiation sequence capable of remaining hybridized under stringent conditions to a T5 promoter sequence, wherein said transcription initiation sequence has at least basal T5 promoter transcriptional activity; (b) at least one regulatory sequence operably linked to said transcription sequence of (a) and capable of remaining hybridized under stringent conditions to a lac operator sequence, wherein said at least one regulatory sequence specifically binds a lacI repressor protein and thereby alters transcriptional activity; (c) at least one cis-acting nucleic acid sequence of about 30 nucleotides; and (d) a translation initiation sequence, was expressed as a soluble polypeptide. As a person of skill in the art will appreciate, the yield and/or production of recombinant proteins may be increased when produced in soluble form, which may also aid in purification procedures. In one preferred embodiment, an expression vector comprising a nucleic acid expression control sequence of the present invention and operably linked to a polynucleotide coding sequence, when introduced into an appropriate host cell, is capable of expressing polypeptide(s) that are in soluble form or insoluble form, preferably in soluble form.

Also provided are methods for producing recombinant polypeptides using the nucleic acid expression control sequences of this invention. That is, any of the nucleic acid molecules and host cells described herein may be used. In a preferred embodiment, a method of producing a recombinant polypeptide comprises culturing a host cell containing a nucleic acid expression vector comprising at least one expression control sequence operably linked to a nucleic acid molecule encoding a recombinant polypeptide under conditions permitting expression of the polypeptide. In another preferred embodiment, the culture may also be contacted with an inducing agent, such as IPTG when the lacO operator is a part of the nucleic acid expression control sequence. As described herein and will be appreciated by those with skill in the art, polypeptides expressed using the nucleic acid expression control sequence of this invention include without limitation a bacteriophage polypeptide, a bacterial polypeptide, a fungal polypeptide, a viral polypeptide, an insect polypeptide, a plant polypeptide, and a mammalian polypeptide. In one particularly preferred embodiment, an immunogenic hybrid polypeptide is produced by this method, and more preferably the immunogenic hybrid polypeptide comprises a hybrid multivalent group A streptococcal M polypeptide. In another preferred embodiment, the immunogenic hybrid polypeptide produced by this method comprises a hybrid polypeptide of *Yersinia pestis* polypeptides F1 and V. In another preferred embodiment, the expression vector pT5 (SEQ ID NO:1) is used in any of the aforementioned methods.

The following examples are offered by way of illustration and not by way of limitation.

EXAMPLES

Example 1

Generation of Modified T5 Promoter/Lac Operator Control Sequence

Figure 2:
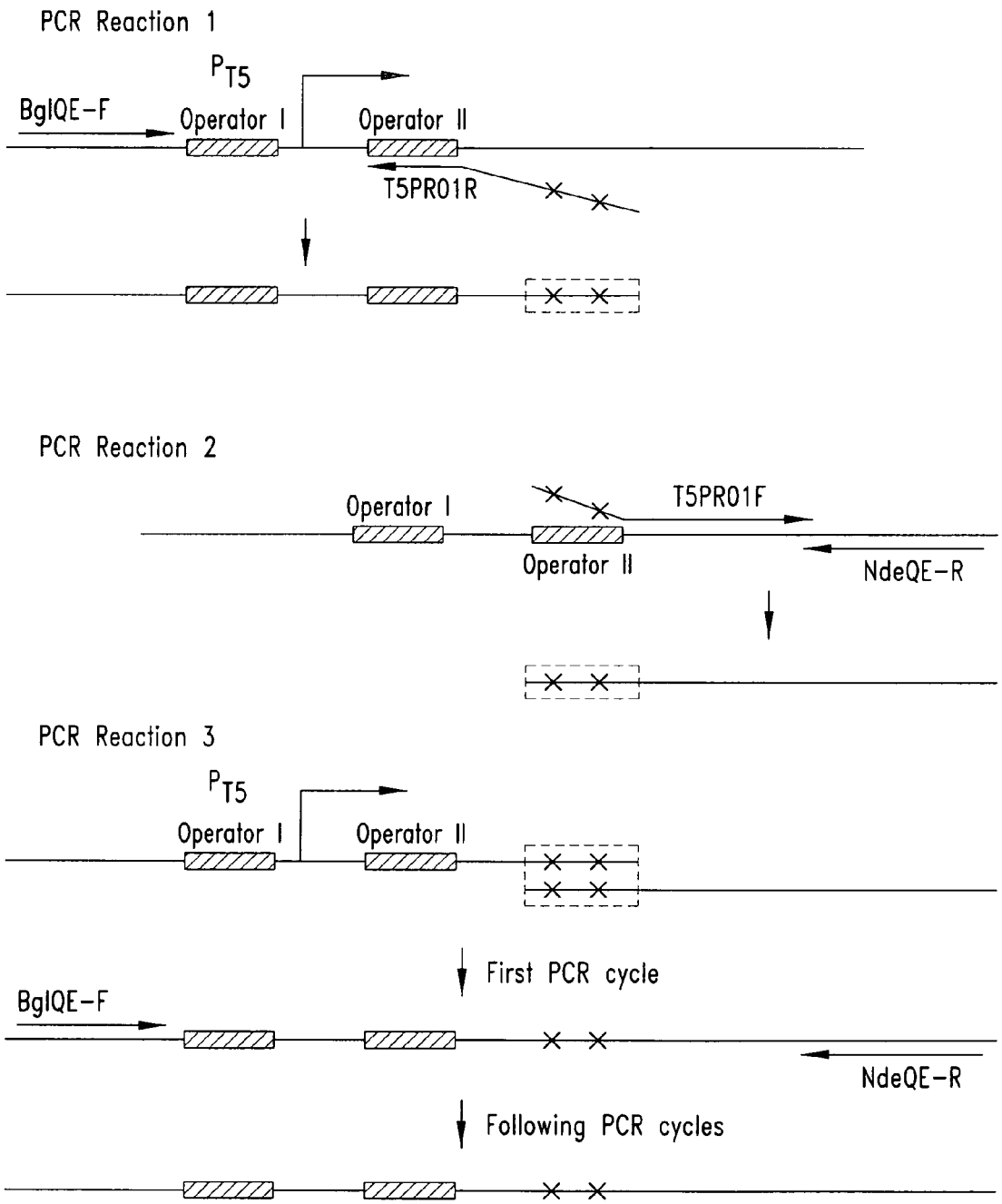
FIG. 2 shows a schematic diagram of the process for making one embodiment of a modified T5 promoter and lac operator using PCR. This series of reactions results in a T5 promoter operably linked to at least two functional lac operators followed by a mutated lac operator (that can no longer function as an operator). Primers BglQE-F (SEQ ID NO:7) and T5PRO1R (SEQ ID NO:10) were used in the first PCR reaction (wherein T5PRO1R primes at operator II), primers NdeQE-R (SEQ ID NO:8) and T5PRO1F (SEQ ID NO:9) were used in the second PCR reaction, and finally primers BglQE-F and NdeQE-R were used to generate SEQ ID NO:2.

The pET-24a plasmid (Novagen, Madison, Wis.) was utilized to create the plasmid pT5. The rhnA gene was cloned into the pET-24a plasmid between the NdeI and BamHI sites to create the plasmid pET-24a-rnhA. The pET-24a plasmid (and pET-24a-rnhA plasmid) contained a T7 promoter/lac operator element downstream from a BgHI restriction endonuclease recognition site and upstream from a multiple cloning site. The T7 promoter/lac operator element between the Bg/II and NdeI sites was then replaced with a T5 promoter/lac operator element that was generated by PCR (see FIG. 3A). The DNA fragment containing mutated bases from Bg/II to NdeI was generated by two rounds of PCR (see FIG. 2) and then inserted into the pET-24a-rnhA plasmid after double digestion with Bg/II and NdeI restriction endonucleases. The resultant pT5-rnhA plasmid was sequenced to verify replacement with the mutated fragment. A fragment of 32 base pairs containing the eight mutated bases was inserted between the lac operator II and the EcoRI site (FIG. 3D). The primer T5PRO1R annealed at operator II during the first round PCR. The nucleotide sequences of PCR templates, primers and products are shown in FIG. 3.

The expression plasmid containing the modified T5 promoter/lac operator expression control sequence has been shown to be very stable and used to consistently express high levels of more than 30 recombinant proteins ranging in molecular mass from 10 kDa to 60 kDa. The protein expression level has been comparable to the protein expression level obtained from the T7 expression system.

Example 2

Cloning and Expression of Recombinant Multivalent Streptococcal Proteins

Figure 4:
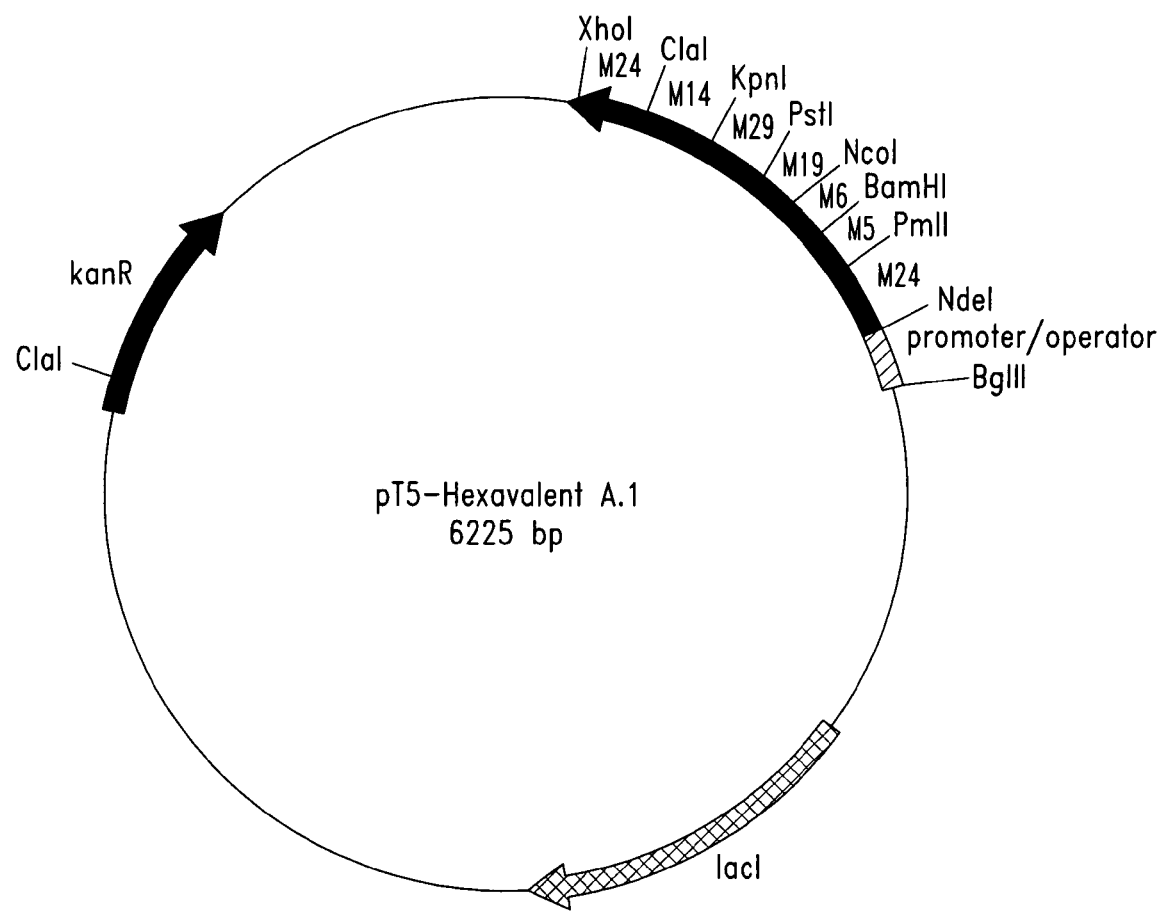
FIG. 4 shows a schematic diagram of plasmid pT5 (SEQ ID NO:1) having the T5 promoter/lac operator control sequence depicted in FIG. 3D operably linked to a nucleic acid sequence that encodes a hexavalent hybrid polypeptide (i.e., hexavalent A.1 is a polypeptide that includes portions of M proteins from different group A streptococci serotypes).
Figure 5:
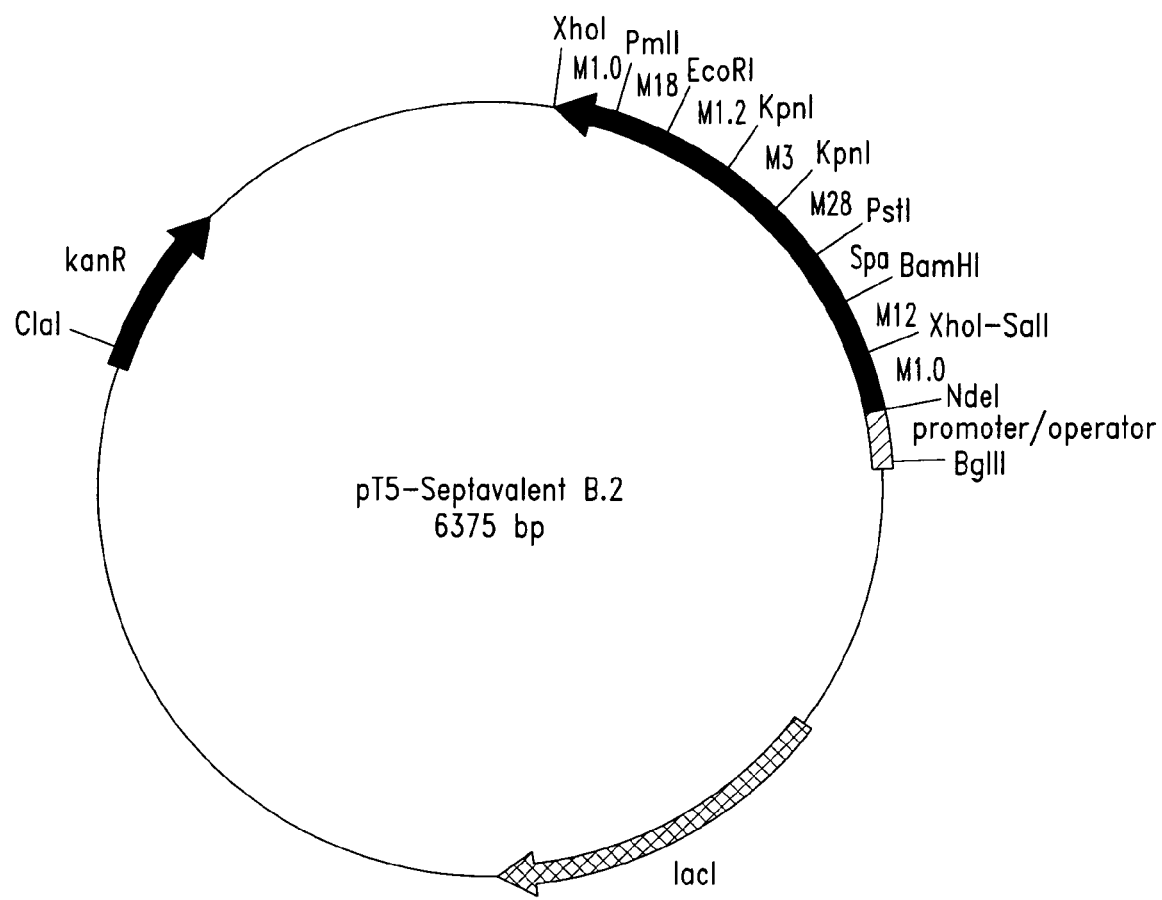
FIG. 5 shows a schematic diagram of plasmid pT5 having the T5 promoter/lac operator control sequence depicted in FIG. 3D operably linked to a nucleic acid sequence that encodes a septavalent hybrid polypeptide (i.e., septavalent B.2 is a polypeptide that includes portions of M proteins from different group A streptococci serotypes).

The specific 5' sequences of each emm and spa gene were used to design hybrid nucleic acid molecules, each containing portions of 6-7 emm and/or spa gene coding sequences linked in tandem by unique restriction enzyme recognition sites. The hybrid nucleic acid molecules were constructed using PCR-generated emm or spa nucleic acid molecules that were amplified from streptococcal genomic DNA of the corresponding serotype using oligonucleotide forward and reverse primers containing restriction enzyme sites at the 5' end. The PCR-generated fragments were purified, digested with the appropriate restriction enzymes, ligated using methods previously described (Dale et. al. *J. Immunol.* 151:2188, 1993: Dale, *Vaccine* 17:193, 1999), and then sequentially cloned into the expression vector pT5. The expression plasmids pT5-Hexavalent A.3 and pT5-Septavalent B.3a were derived from pT5-Hexavalent A.1 (FIG. 4) and pT5-Septavalent B.2 (FIG. 5), respectively, after codon optimization by mutating some of the arginine rare codons AGG or AGA to the high frequency codons CGT or CGC. Each expression plasmid construct of pT5 was used to transform *E. coli* strain JM105. The sequence identity of each hybrid DNA molecule transformed into JM105 *E. coli* was verified by sequencing both strands.

Figure 6:
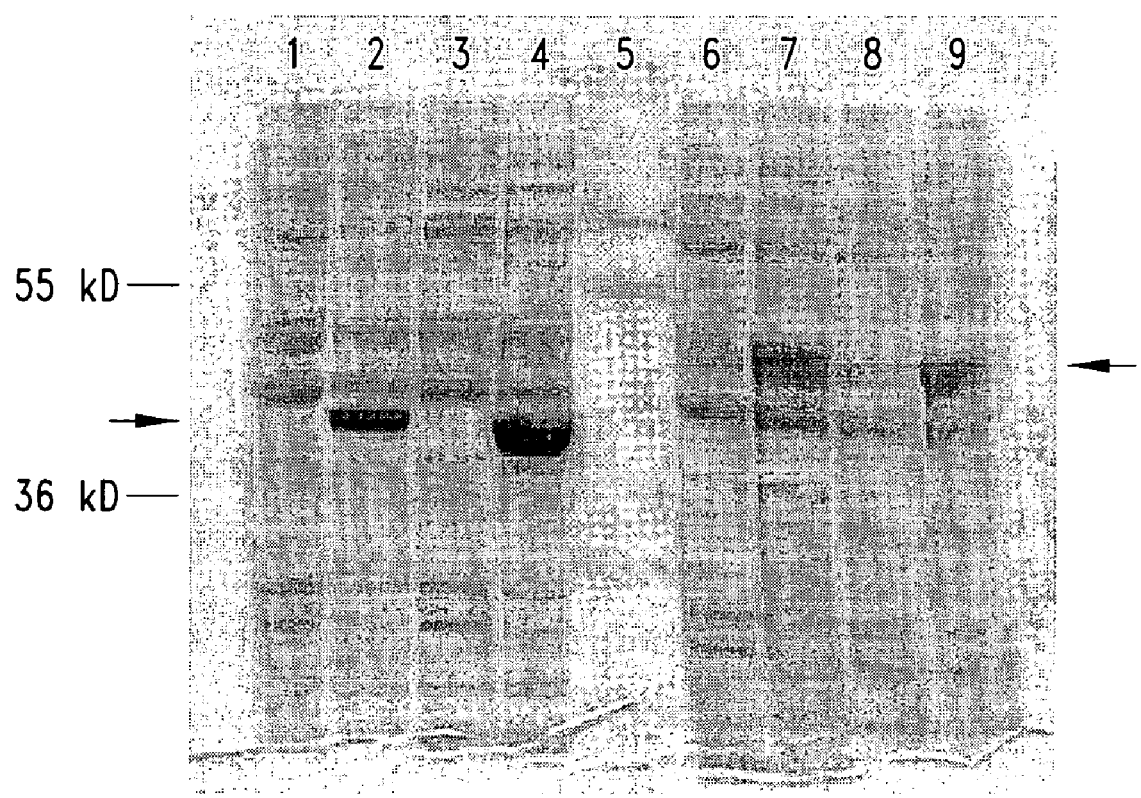
FIG. 6 shows a Coomassie® blue stained SDS-PAGE of whole cell lysates of *Escherichia coli* JM105 containing pT5 constructs grown in the presence or absence of IPTG. Lane 1, uninduced pT5-Hexa A.1; Lane 2, induced pT5-Hexa A.1; Lane 3, uninduced pT5-Hexa A.3; Lane 4, induced pT5-Hexa A.3; Lane 5, standard molecular weight markers (bands corresponding to molecular mass 55 kDa and 36 KDa are shown on the left); Lane 6, uninduced pT5-Septa B.2; Lane 7, induced pT5-Septa B.2; Lane 8, uninduced pT5-Septa B.3a; and Lane 9, induced pT5-Septa B.3a. Hexa A.3 is the same protein as Hexa A.1 and Septa B.3a is the same protein as Septa B.2, except that silent mutations were introduced into the nucleic acid sequence of the 3 series proteins to optimize the codons for expression in *E. coli*. The arrow on the left identifies the overexpressed Hexa A proteins and the arrow on the right identifies the overexpressed Septa B proteins.

Expression of each fusion protein was detected by SDS-PAGE analysis using whole cell lysates before and after 1 mM isopropyl-beta-D-thiogalactopyranoside (IPTG) induction, and staining with Coomassie® blue. These constructs have been and remain very stable. In addition, FIG. 6 shows that there are very high levels of expression for both the Hexavalent A proteins and the Septavalent B proteins. Codon optimization allowed for even higher expression levels.

Example 3

Cloning and Expression of Recombinant Dimeric M18 Streptococcal Proteins

Figure 7:
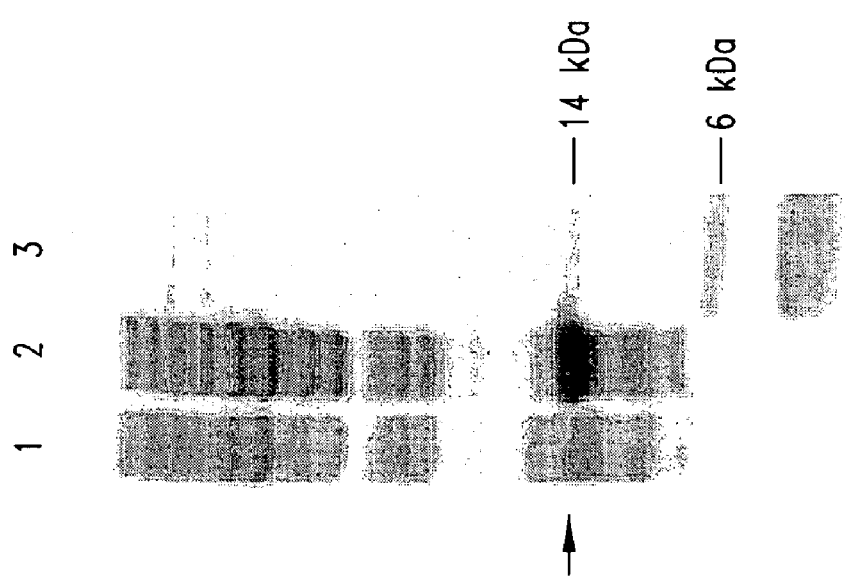
FIG. 7 shows a Coomassie® blue stained SDS-PAGE of whole cell lysates of *Escherichia coli* JM105 containing pT5 constructs grown in the presence or absence of IPTG. Lane 1, uninduced pT5-M18(50aa)-2; Lane 2, induced pT5-M18 (50aa)-2; and Lane 3, standard molecular weight markers (bands corresponding to molecular mass 14 kDa and 6 KDa are shown on the right). The M18(50aa)-2 indicates that a nucleic acid sequence encoding a dimer of the first 50 amino acids from group A streptococci M protein from serotype 18. The arrow on the left identifies the overexpressed M18 dimer.

The emm18 gene fragment coding for the first 50 amino acid residues was amplified by PCR, purified, and cloned sequentially into the expression vector pT5 as an in-frame dimer with a restriction enzyme site (EcoRI) between each coding sequence. The PCR-generated sequence was verified by sequencing both strands of the dimer-encoding nucleic acid molecule. High-level expression of the M18 dimeric peptide in transformed JM105 *E. coli* was detected by SDS-PAGE analysis using whole cell lysates before and after 1 mM isopropyl-beta-D-thiogalactopyranoside (IPTG) induction (FIG. 7). These results show that small polypeptides may be used with the nucleic acid expression control sequence of the present invention.

Example 4

Cloning and Expression of Recombinant Plague Antigen F1-V Fusion Protein

Figure 8:
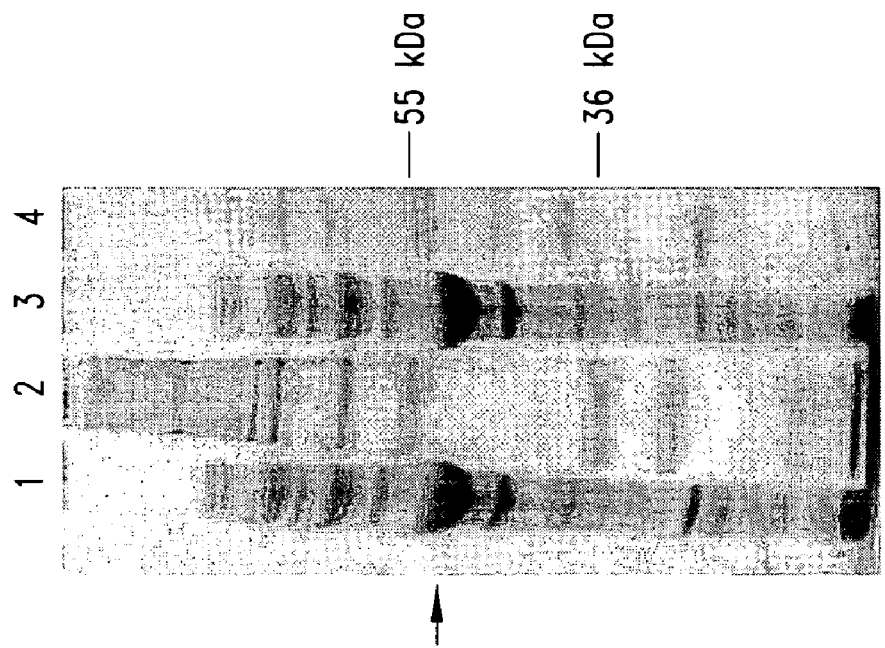
FIG. 8 shows a Coomassie® blue stained SDS-PAGE of different cell fractions of *Escherichia coli* JM105 containing pT5-F1-V grown in the presence of IPTG. Lane 1, whole cell lysate; Lane 2, standard molecular weight markers (bands corresponding to molecular mass 55 kDa and 36 KDa are shown on the right); Lane 3, soluble fraction from the whole cell lysate; and Lane 4, insoluble fraction from the whole cell lysate. F1-V is a fusion protein of two *Yersinia pestis* virulence proteins. The arrow on the left identifies the overexpressed F1-V fusion protein.

The coding sequence of the plague antigen F1-V fusion protein was located between the NdeI and SalI restriction enzyme sites in the plasmid pPW731, which is a T7 expression vector (provided by Dr. Jeffrey Adamovicz at the U.S. Army Medical Research Institute of Infectious Diseases; Heath et al. *Vaccine* 16:1131, 1998). After digestion with the NdeI and SalI restriction enzymes, the coding sequence was purified and cloned into the expression vector pT5 between the NdeI and XhoI sites because the SalI and XhoI sites have compatible ends after the restriction enzyme digestion. The coding sequence of the F1-V fusion protein in the expression vector pT5 was then verified by sequencing both strands. Expression of the F1-V fusion protein in transformed JM105 *E. coli* was detected by SDS-PAGE analysis using whole cell lysates before and after 1 mM isopropyl-beta-D-thiogalactopyranoside (IPTG) induction (FIG. 8). The soluble and insoluble fractions were separated by centrifugation after cells were lysed by microfluidization. Surprisingly, the plague F1-V fusion protein antigen localized to the soluble fraction. When expressed with the T7 expression system, this fusion appeared in the insoluble fraction, even though comparable levels of the fusion protein were expressed from pT5. Thus; when desired, the nucleic acid expression control sequence of the present invention may be useful for producing recombinant proteins in soluble form to aid in isolation, efficiency in yield, and increased production.

All the above U.S. patents, U.S. patent application publications, U.S. patent applications, foreign patents, foreign patent applications, and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A nucleic acid expression control sequence cassette comprising a nucleotide sequence that is at least 95% identical to the nucleotide sequence set forth in SEQ ID NO:2, wherein the nucleotide sequence comprises (a) a lac operator sequence to which a lacI repressor protein specifically binds (b) a mutated lac operator sequence to which a lacI repressor protein cannot specifically bind (c) a T5 promoter sequence; and (d) a translation initiation sequence, wherein the nucleotide sequence controls transcription of an operably linked nucleic acid coding sequence, and wherein the nucleotide sequence is stable in *E. coli* and provides high level expression of a polypeptide encoded by the nucleic acid coding sequence.

2. The cassette according to claim 1, wherein the a nucleotide sequence is at least 97% identical to the nucleotide sequence set forth in SEQ ID NO:2.

3. A nucleic acid expression vector comprising the nucleic acid expression control sequence cassette according to either claim 1 or claim 2.

4. The expression vector according to claim 3 wherein the polypeptide is selected from a bacteriophage polypeptide, a bacterial polypeptide, a fungal polypeptide, a viral polypeptide, and insect polypeptide, a plant polypeptide, and a mammalian polypeptide.

5. The expression vector according to claim 4 wherein the polypeptide is an immunogenic hybrid polypeptide comprising at least one bacterial polypeptide.

6. The expression vector according to claim 5 wherein the immunogenic hybrid polypeptide comprises a hybrid multivalent group A streptococcal M polypeptide.

7. The expression vector according to claim 5 wherein the immunogenic hybrid polypeptide comprises a hybrid polypeptide of *Yersinia pestis* polypeptides F1 and V.

8. The expression vector according to claim 3 wherein the nucleic acid coding sequence further comprises a nucleotide sequence that encodes an identification peptide, wherein the peptide is fused in-frame to the polypeptide encoded by the nucleic acid coding sequence.

9. The expression vector according to claim 8 wherein the peptide is fused in-frame to the amino terminal end of the polypeptide or to the carboxy terminal end of the polypeptide.

10. A host cell comprising the expression vector according to claim 3.

11. The host cell according to claim 10 wherein the host cell is selected from a bacterium, a fungus, an insect cell, a plant cell, and a mammalian cell.

12. The host according to claim 10 wherein the host cell is a bacterium.

13. A method for producing the polypeptide, comprising:
    a) culturing the host cell according to claim 10 under conditions sufficient to express the polypeptide encoded by the nucleic acid coding sequence; and
    b) isolating the polypeptide.

14. The method according to claim 13 wherein the polypeptide is in soluble form.

15. The method according to claim 13 wherein the polypeptide is selected from a bacteriophage polypeptide, a bacterial polypeptide, a fungal polypeptide, a viral polypeptide, an insect polypeptide, a plant polypeptide, and a mammalian polypeptide.

16. The method according to claim 13 wherein the polypeptide comprises a hybrid multivalent group A streptococcal M polypeptide.

17. The method according to claim 13 wherein the polypeptide comprises a hybrid polypeptide of *Yersinia pestis* polypeptides F1 and V.

18. The method according to claim 13 wherein the polypeptide further comprises an identification peptide that is fused in-frame to the amino-terminal end or the carboxy terminal end of the polypeptide.

19. The method according to claim 13 wherein the host cell is selected from a bacterium, a fungus, an insect cell, a plant cell, and a mammalian cell.

20. The method according to claim 13 wherein the host cell is a bacterium.

21. A host cell comprising an expression vector that comprises the polynucleotide sequence set forth in SEQ ID NO:1.

* * * * *

UNITED STATES PATENT AND TRADEMARK OFFICE
CERTIFICATE OF CORRECTION

PATENT NO. : 7,528,245 B2  Page 1 of 1
APPLICATION NO. : 11/209589
DATED : May 5, 2009
INVENTOR(S) : Mary ChaoHung Hu It is certified that error appears in the above-identified patent and that said Letters Patent is hereby corrected as shown below:

Column 25
Line 64, "specifically bind (c) a" should read --specifically bind; (c) a--.

Column 26
Line 60, "wherein the a nucleotide" should read --wherein the nucleotide--.

Column 27
Line 30, "The host according" should read as --The host cell according--.

Signed and Sealed this

Twenty-fifth Day of May, 2010

David J. Kappos
*Director of the United States Patent and Trademark Office*

SEQUENCE LISTING

<160> NUMBER OF SEQ ID NOS: 13

<210> SEQ ID NO 1
<211> LENGTH: 5347
<212> TYPE: DNA
<213> ORGANISM: Artificial Sequence
<220> FEATURE:
<223> OTHER INFORMATION: Vector plasmid pT5

<400> SEQUENCE: 1

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttttagg    180 gttccgattt agtgctttac ggcacctcga ccccaaaaaa cttgattagg gtgatggttc     240
acgtagtggg ccatcgccct gatagacggt ttttcgccct tgacgttgg agtccacgtt     300 ctttaatagt ggactcttgt tccaaactgg aacaacactc aaccctatct cggtctattc     360
ttttgattta taagggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
```

```
gatccttttt ttctgcgcgt aatctgctgc ttgcaaacaa aaaaaccacc gctaccagcg   1560
gtggtttgtt tgccggatca agagctacca actcttttc cgaaggtaac tggcttcagc    1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccggggttg gactcaagac gatagttacc ggataaggcg   1800
cagcggtcgg gctgaacggg gggttcgtgc acacagccca gcttggagcg aacgacctac   1860
accgaactga gataacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt cctgcgtta    2160 tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280 tatttctcc ttacgcatct gtgcggtatt tcacaccgca tatatggtgc actctcagta    2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
```

```
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatcta atcataaaaa    4980
atttatttgc tttgtgagcg gataacaatt ataatagatt caattgtgag cggataacaa    5040
ttataataga ttcaattcta aatttacaag aatttcacac agaattcatt aaagaggaga    5100
aattacatat ggctagcatg actggtggac agcaaatggg tcgcggatcc gaattcgagc    5160
tccgtcgaca gcttgcggc cgcactcgag caccaccacc accaccactg agatccggct    5220
gctaacaaag cccgaaagga agctgagttg gctgctgcca ccgctgagca ataactagca    5280
taaccccttg gggcctctaa acgggtcttg agggttttt tgctgaaagg aggaactata    5340
tccggat                                                              5347

<210> SEQ ID NO 2
<211> LENGTH: 166
<212> TYPE: DNA
<213> ORGANISM: Artificial Sequence
<220> FEATURE:
<223> OTHER INFORMATION: Modified promoter/operator region

<400> SEQUENCE: 2
gaagatctaa atcataaaaa atttatttgc tttgtgagcg gataacaatt ataatagatt     60
caattgtgag cggataacaa ttataataga ttcaattcta aatttacaag aatttcacac    120
agaattcatt aaagaggaga aattacatat gaatccatca cctaga                   166

<210> SEQ ID NO 3
<211> LENGTH: 134
<212> TYPE: DNA
<213> ORGANISM: Artificial Sequence
<220> FEATURE:
<223> OTHER INFORMATION: Modified promoter/operator region

<400> SEQUENCE: 3
gaagatctaa atcataaaaa atttatttgc tttgtgagcg gataacaatt ataatagatt     60
```

```
caattctaaa tttacaagaa tttcacacag aattcattaa agaggagaaa ttacatatga      120
atccatcacc taga                                                       134

<210> SEQ ID NO 4
<211> LENGTH: 138
<212> TYPE: DNA
<213> ORGANISM: Artificial Sequence
<220> FEATURE:
<223> OTHER INFORMATION: Promoter/operator region

<400> SEQUENCE: 4
agatctaaat cataaaaaat ttatttgctt tgtgagcgga taacaattat aatagattca       60
attgtgagcg gataacaatt tcacacagaa ttcattaaag aggagaaatt acatatgaat      120
ccatcaccta gaaaacgc                                                   138

<210> SEQ ID NO 5
<211> LENGTH: 138
<212> TYPE: DNA
<213> ORGANISM: Artificial Sequence
<220> FEATURE:
<223> OTHER INFORMATION: Modified promoter/operator region

<400> SEQUENCE: 5
agatctaaat cataaaaaat ttatttgctt tgtgagcgga taacaattat aatagattca       60
attctaaatt tacaagaatt tcacacagaa ttcattaaag aggagaaatt acatatgaat      120
ccatcaccta gaaaacgc                                                   138

<210> SEQ ID NO 6
<211> LENGTH: 170
<212> TYPE: DNA
<213> ORGANISM: Artificial Sequence
<220> FEATURE:
<223> OTHER INFORMATION: Modified promoter/operator region

<400> SEQUENCE: 6
agatctaaat cataaaaaat ttatttgctt tgtgagcgga taacaattat aatagattca       60
attgtgagcg gataacaatt ataatagatt caattctaaa tttacaagaa tttcacacag      120
aattcattaa agaggagaaa ttacatatga atccatcacc tagaaaacgc                170

<210> SEQ ID NO 7
<211> LENGTH: 30
<212> TYPE: DNA
<213> ORGANISM: Artificial Sequence
<220> FEATURE:
<223> OTHER INFORMATION: BglQE-F primer

<400> SEQUENCE: 7
gaagatctaa atcataaaaa atttatttgc                                       30

<210> SEQ ID NO 8
<211> LENGTH: 33
<212> TYPE: DNA
<213> ORGANISM: Artificial Sequence
<220> FEATURE:
<223> OTHER INFORMATION: NdeQE-R primer

<400> SEQUENCE: 8
tctaggtgat ggattcatat gtaatttctc ctc                                   33

<210> SEQ ID NO 9
<211> LENGTH: 49
```

```
<212> TYPE: DNA
<213> ORGANISM: Artificial Sequence
<220> FEATURE:
<223> OTHER INFORMATION: T5PRO1F primer

<400> SEQUENCE: 9
tagattcaat tctaaattta caagaatttc acacagaatt cattaaaga            49

<210> SEQ ID NO 10
<211> LENGTH: 48
<212> TYPE: DNA
<213> ORGANISM: Artificial Sequence
<220> FEATURE:
<223> OTHER INFORMATION: T5PRO1R  primer

<400> SEQUENCE: 10
cttgtaaatt tagaattgaa tctattataa ttgttatccg ctcacaaa             48

<210> SEQ ID NO 11
<211> LENGTH: 117
<212> TYPE: DNA
<213> ORGANISM: Artificial Sequence
<220> FEATURE:
<223> OTHER INFORMATION: Promoter/operator region

<400> SEQUENCE: 11
gtatacatta aagaggagaa attacttaag acacacttta acaataggcg agtgttaact    60
tagataatat taacaatagg cgagtgtttc gtttatttaa aaaatactaa atctaga      117

<210> SEQ ID NO 12
<211> LENGTH: 8
<212> TYPE: PRT
<213> ORGANISM: Artificial Sequence
<220> FEATURE:
<223> OTHER INFORMATION: Carboxy terminal tag sequence

<400> SEQUENCE: 12

Asp Tyr Lys Asp Asp Asp Asp Lys
 1               5

<210> SEQ ID NO 13
<211> LENGTH: 8
<212> TYPE: PRT
<213> ORGANISM: Artificial Sequence
<220> FEATURE:
<223> OTHER INFORMATION: Carboxy terminal tag sequence

<400> SEQUENCE: 13

Asp Leu Tyr Asp Asp Asp Asp Lys
 1               5
```